(12) United States Patent
Springub

(10) Patent No.: US 10,603,567 B2
(45) Date of Patent: Mar. 31, 2020

(54) ALIGNMENT AID FOR A GOLFER

(71) Applicant: Georg Springub, Altenberge (DE)

(72) Inventor: Georg Springub, Altenberge (DE)

( * ) Notice: Subject to any disclaimer, the term of this patent is extended or adjusted under 35 U.S.C. 154(b) by 285 days.

(21) Appl. No.: 15/127,180

(22) PCT Filed: Mar. 17, 2015

(86) PCT No.: PCT/EP2015/000582
§ 371 (c)(1),
(2) Date: Apr. 19, 2018

(87) PCT Pub. No.: WO2015/139832
PCT Pub. Date: Sep. 24, 2015

(65) Prior Publication Data
US 2018/0214759 A1 Aug. 2, 2018

(30) Foreign Application Priority Data
Mar. 18, 2014 (DE) .......... 10 2014 103 681

(51) Int. Cl.
*A63B 69/36* (2006.01)
*A43B 3/00* (2006.01)
(Continued)

(52) U.S. Cl.
CPC ........ *A63B 69/3667* (2013.01); *A43B 3/0005* (2013.01); *A43B 5/001* (2013.01); *A61B 5/0024* (2013.01); *A61B 5/11* (2013.01); *A61B 5/1112* (2013.01); *A61B 5/1114* (2013.01); *G01C 21/20* (2013.01); *A61B 5/1116* (2013.01); *A61B 5/6807* (2013.01); *A61B 5/6828* (2013.01); *A61B 5/6829* (2013.01);

*A61B 5/742* (2013.01); *A61B 5/7415* (2013.01); *A61B 5/7455* (2013.01); *A61B 2503/10* (2013.01); *A63B 57/00* (2013.01); *A63B 69/3608* (2013.01); *A63B 69/3623* (2013.01); *A63B 71/06* (2013.01); *A63B 71/0622* (2013.01); *A63B 2071/0625* (2013.01); *A63B 2071/0655* (2013.01); *A63B 2220/12* (2013.01); *A63B 2220/16* (2013.01); *A63B 2220/836* (2013.01); *A63B 2225/50* (2013.01)

(58) Field of Classification Search
CPC ..................................................... A63B 69/36
See application file for complete search history.

(56) References Cited

U.S. PATENT DOCUMENTS

| 7,602,301 B1 | 10/2009 | Stirling et al. |
| 2007/0265105 A1 | 11/2007 | Barton et al. |

(Continued)

FOREIGN PATENT DOCUMENTS

| WO | 2012027726 A2 | 3/2012 |
| WO | 2012138605 A2 | 10/2012 |

*Primary Examiner* — Omkar A Deodhar
(74) *Attorney, Agent, or Firm* — Dinsmore & Shohl LLP

(57) ABSTRACT

An alignment aid for a golfer includes a handheld device with a direction finding device for determining a target vector (V1) with respect to a sighted target, a sensor device for determining a position vector (V2) as a measure of an instantaneous alignment of the golfer, and a display device. The alignment aid is operable to check an included angle (a) between the target vector (V1) and the position vector (V2) and to output a good signal (G) to the display device upon a successful check of the included angle.

16 Claims, 4 Drawing Sheets

(51) Int. Cl.
*A43B 5/00* (2006.01)
*G01C 21/20* (2006.01)
*A61B 5/11* (2006.01)
*A61B 5/00* (2006.01)
*A63B 71/06* (2006.01)
*A63B 57/00* (2015.01)

(56) References Cited

U.S. PATENT DOCUMENTS

| | | |
|---|---|---|
| 2009/0137933 A1 | 5/2009 | Lieberman et al. |
| 2009/0143882 A1 | 6/2009 | Young |
| 2010/0099509 A1 | 4/2010 | Ahem et al. |
| 2010/0179005 A1* | 7/2010 | Meadows ............... G01S 19/19 473/407 |
| 2011/0230274 A1 | 9/2011 | Lafortune et al. |

* cited by examiner

ALIGNMENT AID FOR A GOLFER

CROSS-REFERENCE TO RELATED APPLICATIONS

This application is a U.S. National phase application of International application no. PCT/EP2015/000582, which was filed on Mar. 17, 2015 and which claims priority of German application no. 10 2014 103 681.6, which was filed on Mar. 18, 2014; both of which are incorporated herein by reference.

FIELD OF THE INVENTION

The invention relates to an alignment aid for a golfer.

BACKGROUND OF THE INVENTION

It is necessary to be able to play a stroke of the golf ball in the direction of the sighted target, for example a hole on the green of a course that the player positions himself correctly for the stroke. In this respect, the feet, knees, hips, eyes and shoulders have to be aligned in parallel with a line in the direction of the sighted target. The face of the club should be aligned exactly on the target. If the golfer stands with an incorrect alignment, the ball may pass the sighted target to the side when striking the ball.

Most mistakes in a golf swing result from an incorrect alignment, with the largest alignment problem being the manner the target is sighted. As soon as one stands laterally to the target and wants to hit one's golf ball, the right eye becomes more dominant when one turns and inclines one's head to look toward the target. The visual line, that is the straight line between the eye and the fixated target, is thereby deflected further to the right than it actually is and thus naturally produces an optical illusion. As a result of this, the feet, knees, hips, eyes and shoulders are then often not aligned in parallel with the target line.

Systems and methods for the provision of coaching and training information specific to golf to individual golfers are described in WO 2012/138605 A2 and are based on data which are produced during individual golf strokes. This golf stroke analyzing system comprises a data acquisition and storage apparatus which receives data from a GPS system, from the golf club, from the golf shoes and from a clothing component such as a golf glove or shirt, which processes said data and which forwards them via a network to a portable electrical device and/or to a data hub where the data are stored, analyzed and displayed. In this respect, the data acquisition and storage apparatus can be attached to a golf cart or to a golf bag to which a video camera, an alignment aid such as a laser, a tilt sensor and so on can be attached. Sensors for detecting force data are provided in the shoes, whereas sensors for detecting position data are provided in the golf club and in the clothing component to determine the position of the body part, such as the hands or shoulders, or of the golf club. Such a system and the methods are, however, only adapted to analyze a golf club during or after the execution of this golf stroke. No advance indications for optimizing a specific stroke are possible here.

A portable wireless mobile device is disclosed as a movement detection and analysis system in WO 2012/027726 A2 which comprises at least one movement detection element for coupling with the golfer or with his equipment and an application on a mobile device. The movement detection element comprises a WIFI measuring unit and can be attached to a golf shoe, to sunglasses, to the club face or in the handle of a golf club to detect any combination of position values, speed values and acceleration values. The system and the methods are in this respect also adapted for analyzing a golf stroke during or after the execution of a specific golf stroke or for displaying a training plan. No advance indications for optimizing a specific stroke are possible here either. The movement detection and analysis system is thus not suitable as an alignment aid for golfers before the stroke.

An analysis device for strokes with a golf club is described in the patent application US2010/0099509 A1 in which sensors in the golf club and in a glove deliver signals on the current stroke and said stroke is analyzed in a display device. The determination of a vector to the target is not carried out.

An analysis device for the holding and the stroke of a golf club is described in the patent application US2007/0265105 A1. Three light sources, which are observed and analyzed by a camera, are installed at the golf club for this purpose. The determination of a vector to the target is not carried out.

It is disclosed in the "Alignment Aid Tool" of the iPhone application "Golf Tools Pro" of Brendan Magill (http://www.appticker.de/ch/app/585644/golf-tools-pro.html) that the iPhone is used as a gyroscope to align the feet of a golfer with a selected target. In this respect, in a first step, the target line is sighted by direction finding using a direction marking line on the iPhone screen and is stored. In a second step, a position line and position marks for the feet of the golfer are then shown on the screen which additionally have the image currently recorded by the rear camera of the iPhone superposed on them. In this respect, however, handling is extremely difficult in practice. The iPhone device has to be held with at least one hand with the camera directed to the ground for the alignment of the feet of the golfer. At the same time, the two feet have to be brought into alignment with the position marking or the position line via the current image shown on the screen. The golfer can accordingly not adopt the stroke position in which the grip of the club is fixedly gripped with both hands to propel the golf ball in the direction of the hole in a swing movement, with the club face being aligned by 90° toward the target line.

SUMMARY OF THE INVENTION

It is the underlying problem of the invention to provide an alignment aid for a golfer which is easy to handle and simple to transport.

The invention solves this problem by an alignment aid having the features described herein and by a method having the features described herein. Advantageous aspects and further developments of the invention are also described.

A reliable aid for the golfer is provided by the invention in that the alignment aid for aligning the golfer in the direction of a sighted target comprises a handheld device having a direction finding device for determining a target vector with respect to the sighted target as well as a sensor device for determining a position vector as a measure of the instantaneous alignment of the golfer and in that it comprises means for checking an included angle between the target vector and the position vector and in that a good signal can be output on a display device on a successful check. Said aid simply determines only a first vector with respect to the target as well as a second, actual vector of the alignment of the golfer. If these two vectors are in alignment, the alignment is correct and the stroke can be carried out.

If the alignment of a horizontal body line of the golfer can advantageously be detected by the sensor device, further error vectors are disabled.

The sensor device can, for example, be formed externally by a ruler or similar which can be held at the ground, which is aligned by the feet of the golfer and whose angle with respect to the target vector can thereby be changed. The contact of the feet can then be confirmed by contact sensors or the like and the golfer can align himself thereat. In function, the sensor device is then in contact with the golfer so that his alignment then necessarily corresponds to the alignment of the sensor device.

For a visually unobtrusive holding, the sensor device in particular comprises a single sensor for the body alignment such as an electronic compass or, for high security and a reliable alignment, at least two sensor systems which are arranged in or at the body and/or in or at the clothing of the golfer. This can, for example, be a sensor systems at hook and loop strips which can be held around the heel or midfoot; alternatively, such hook and loop strips can be held around the knee or around the lower legs, for instance hidden by socks and trousers (or with a little less security at the hips or shoulders).

A special advantage of the invention is that it functional before the striking of a golf ball and therefore does not analyze errors in retrospect, but rather optimizes the specific stroke in advance. This optimization does not take place using statistical data, but rather the very specific body posture for the respective stroke.

The handheld device can comprise a direction finding device having a direction sensor for determining a target vector to the sighted target. In this respect, the target can be a hold on a green with a straight fairway or also a first directional point with a kinked fairway having a dogleg. In the drawn embodiment, the first and second sensor systems furthermore have a respective direction sensor in the first and second shoes for determining a position vector between the first and second shoes. These sensor systems are visually very unobtrusive and can be installed as modules themselves in the respective shoe. Furthermore, the handheld device here comprises means for checking the included angle between the target vector and the position vector. The included angle is always the smaller angle between the two vectors and can be calculated using the scalar product. If both shoes of the golfer are aligned ideally in parallel with the target vector in this version, a successful check of the included angle with respect to zero is adopted and a good signal is output on a display device.

Alternatively, only one sensor can be provided, for instance in or at a shoe, in particular for advanced players whose foot posture is optimized with respect to the whole body posture without bending.

The display or signaling device can display the ideal alignment visually, acoustically and/or by vibration. In the visual signal, for example, color light-emitting diodes light up in green, yellow or red or a suitable graphical signaling takes place on the screen of a smartphone. With an acoustic signaling, for example, a sound which pulsates from slow to fast is output on a loudspeaker. And with a vibration signaling, the ideal alignment is simply communicated by different vibrations. In addition to the output to a handheld device or smartphone, the invention provides the attachment of a display apparatus to, for example, a shoe or the wrist so that the handling is simple. The transport effort for such an alignment aid is also practically zero.

The direction finding device can favorably comprise a direction finding rod or a direction marking with the aid of which the target can be sighted substantially by the human gaze. In this respect, the relative direction to the target and its angle are measured by the direction sensor in the direction finding device, from which the target vector can be determined. The invention furthermore provides the American GPS system for the determination of the target vector. It is thus possible to localize the location of the GPS receiver. The GPS receiver measures the signal transit times from at least three satellites and calculates its position therefrom for the actual position determination. If the coordinates of the target position, e.g. of the hole on the green, are known, the coordinates of the position of the golfer at the tee can be determined using a GPS receiver in the handheld device or smartphone and the target vector can subsequently be determined therefrom. Or the GPS coordinates of the target are measured first and then the GPS coordinates of the teeing ground so that the target vector can be determined from both GPS coordinates. The data of the target vector are then, for example, stored in the memory of the handheld device or in the sensor devices.

The direction sensors which are used in the direction finding device and in the first and second sensor systems are favorably configured as a microelectromechanical vibratory gyroscope or MEMS gyroscope. These gyroscopes mostly comprise very small mass elements which are set into vibration in one axis and whose movement due to influences of Coriolis force on capacitive elements arranged in a horizontal axis is measured. The MEMS gyroscope is manufactured from a silicon wafer in a similar process as with integrated circuits. The measurement parameters of position, speed and location can be determined by means of suitable integration processes. A high precision can accordingly be achieved in the determination of the relative position by the arrangement of the first and second sensor systems, for example, in the first and second heel region or the heel of the first and second shoes.

The handheld device or smartphone here comprises a first transmission/reception device for a simple, wireless data transmission for the exchange of data via radio with the first and second sensor systems. Different transmission techniques can be used for this purpose such as WIFI or Bluetooth. The first and second sensor systems then comprise respective associated second transmission/reception devices for exchanging data over radio between the first and second sensor systems and with the handheld device. The position vector can hereby be determined by transmitting the relative positions between the two sensor systems in order then subsequently to transmit said position vector to the handheld device where it is stored in the memory of the handheld device. The position vector in this respect runs through the center of the first sensor system and the center of the second sensor system. The data of the position vector are also stored in the memory of the handheld device, for example.

The handheld device or smartphone can furthermore comprise means for checking the included angle between the target vector and the position vector which can in turn be a component of a processing system. This processing system, for example, contains existing software components and/or hardware components of a commercial smartphone. The data of the stored target vector and of the stored position vector are linked in the processing system here and the included angle is determined as the result and the angular dimension is subsequently checked for the value zero. On a successful check, the good signal is output to the desired display device. At the time of the striking of the golf ball, in contrast, the visual, acoustic or vibration signal disturbs the golfer. For this reason, the handheld device or smartphone particularly favorably has a switch or an automatic switch-off-system for switching off the good signal. The automatic switch-off system can be time-controlled. Such a switching off is a requirement to be able also to use the device in tournaments.

The automatic switch-off system can also analyze the position of rest of the feet after an alignment and can then automatically switch the good signal off.

The method in accordance with the invention for checking the included angle between the target vector and the position vector using the alignment aid provides first aligning the direction finding device to the target, whereby the target vector is received by the direction finding device. The position vector is then determined by the sensor device as a measure for the alignment of the golfer. Both the target vector and the position vector are stored in the memory of the handheld device or smartphone. The golfer now aligns himself in parallel with the target vector and the processing system determines the included angle between the target vector and the position vector with reference to the currently received position vector and checks the angular dimension of the included angle. The golfer continues to align his transverse axis, for example via his two shoes, in parallel with the target vector until the included angle becomes equal to zero. The good signal is thereby output by the processing system due to this successful check to the display device, e.g. visual display, acoustic signal and/or vibration signal. The golfer is not forced to hold the handheld device or smartphone in his hands during the alignment; he rather has both hands free to adopt the stroke position in which both hands enclose the grip of the golf club and in which simultaneously the face of the club is aligned by 90° with respect to the target vector. The target vector can optionally be formed from the GPS coordinates of the GPS reception device. The method in accordance with the invention furthermore also provides the switching off of the good signal after a time or by means of the switch at the handheld device or smartphone so that the golfer is not disturbed by the visual, acoustic or vibration signal when carrying out the golf stroke in the direction of the hole or of the first directional point.

Different points of the body characteristic for the direction can particularly advantageously be fixed for the attachment of the first and second sensor systems. As already described in detail, the positions characteristic for the direction can be in the heels of the first and second shoes. Alternatively, the positions characteristic for the direction can be in a first and second shoulder joint region of a shirt or also in a first and second hip joint region of a belt. Preferred further embodiments of the alignment aid provide that the invention is not restricted to the alignment of a golfer before striking a golf ball, but rather can also be used in training systems for other ball sports, for example for mini golf or cricket or also tennis and badminton. It is understood that the system configuration is then adapted overall to the typical movement routines in the respective sport.

BRIEF DESCRIPTION OF THE DRAWINGS

The invention is described in the following by way of example with reference to preferred embodiments and to the Figures.

DETAILED DESCRIPTION OF THE INVENTION

Figure 1:
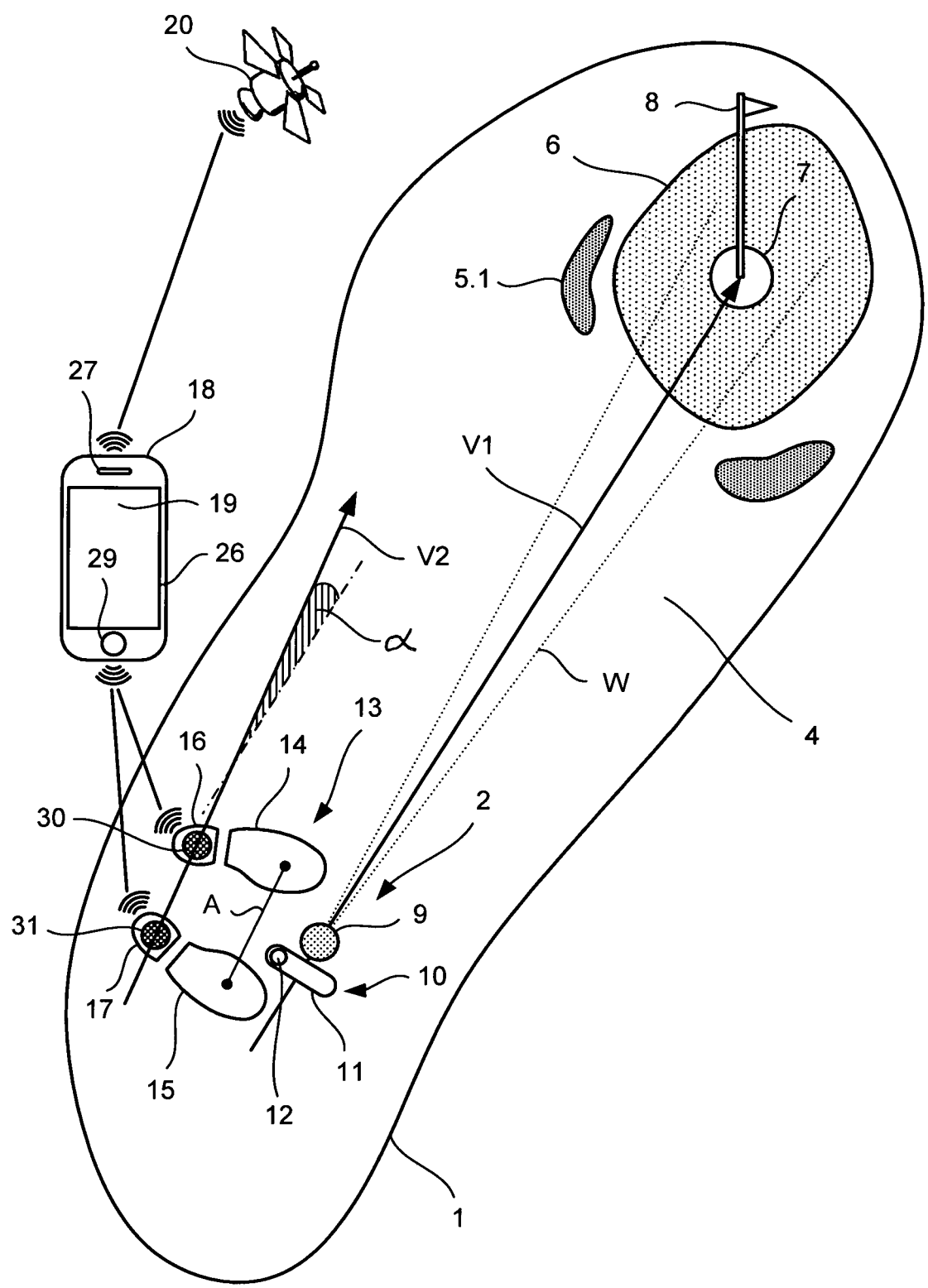
FIG. 1 is a schematic showing an exemplary embodiment of an alignment aid in accordance with the invention—here with two sensors in two shoes—in a state aligned relative to a hole.

FIG. 1 shows a plan view of a course 1 with a straight fairway 4. The teeing ground 2 is arranged at the bottom end of the course 1 with a green 6 arranged at the oppositely disposed end. The green 6 is the target zone in golf on which the golf ball is propelled in the direction of the hole 7. Such a hole 7 comprises a cylindrical cup which is let into the surface of the green 6 in which the flagstick 8 stands to whose upper end a flag is fastened. Hazards frequently lie around the green 6 and are intended to make the approach more difficult. They are often sand bunkers 5.1 which can be extremely deep; but water hazards are also typical.

The teeing ground 2 is a planar grass area which is usually rectangular and often slightly raised. A teeing mark within this area indicates the position from which the gold ball 9 has to be struck. The significance of the correct alignment of the feet, knees, hips, eyes and shoulders in parallel with the target line or target vector V1 is particularly important to propel the golf ball 9 as close as possible to the hole 7. In this respect, the eyes of the golfer 13 are directed directly over the golf ball 9 and the target line or target vector V1. The golfer 13 therefor has to have the feeling during this stroke that his body is aligned correctly in parallel with the target 7. When teeing off, the club face 11 is ideally exactly directed to the target or hole 7. In so doing, the golfer 13 surrounds the grip at the upper end of the shaft 12 of the golf club 10 with both hands and aligns the club face 11 by 90° with respect to the target line or target vector. However, for many golfers 13, the largest alignment problem is the way they sight the target 7. For example, the body of the golfer 13 is aligned to the target in that they hold the golf club 10 transversely over the hips and then look where the it faces. Even a small deviation in the parallel alignment of the body results through the golf stroke over a long distance to a significant deviation W from the ideal target line or target vector V1.

The alignment aid in accordance with the invention assists the golfer 13 in the correct alignment of the body to the target vector V1 which is determined by a GPS direction finding 20 with the aid of the direction finding device 19 in the handheld device 18 and is saved. Furthermore, a first and second sensor system 30, 31 are arranged in the first and second heel regions 16, 17 of the first and second shoes 14, 15 of the golfer 13 by which the position vector V2 is determined which is in turn transmitted by radio to the handheld device 18 where it is stored. In this respect, the two shoes 14, 15 are placed at a spacing A from one another which approximately corresponds to the shoulder width of the body.

The included angle a between the target vector V1 and the position vector V2 is determined in the handheld device 18 and its angular dimension is checked. When the two shoes 14, 15 are aligned exactly in parallel with the target vector V1, the angular dimension of the included angle a is equal to zero and a good signal G is output on the visual signal 26 and/or on the acoustic signal 27. The good signal G can be switched off after a time or by means of the switch 29 in order not to disturb the golfer when carrying out the golf stroke and to be able to observe the rules of a tournament.

Figure 2:
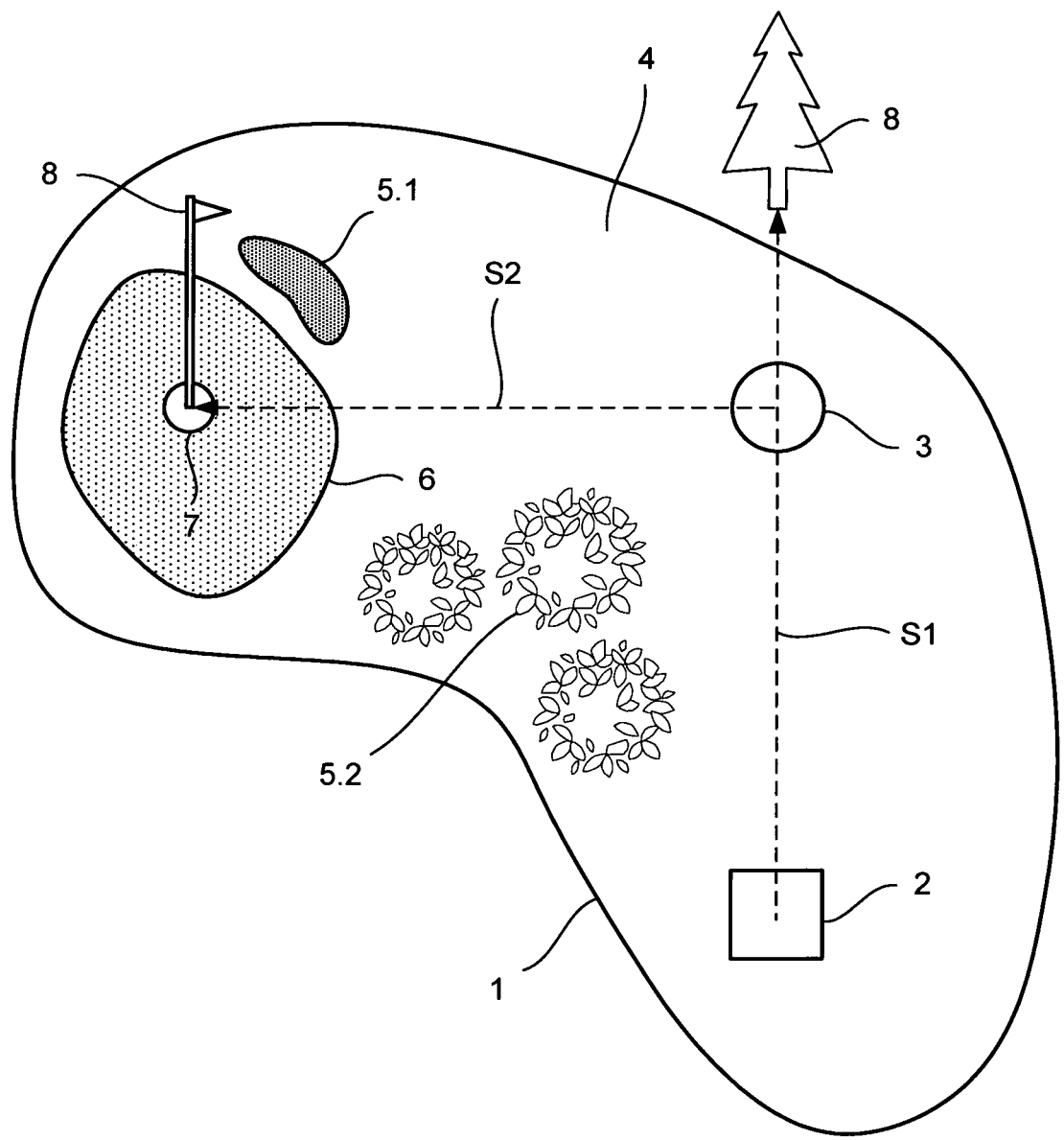
FIG. 2 is a schematic showing a plan view of an angled course with a first directional point.

FIG. 2 shows a plan view of an angled course 1 whose fairway 4 is curved or bent to the left. The change of direction is approximately at the point at which a good first golf stroke S1 should land from the tee 2. In addition, due to a planting 5.2 of the fairway 4 with trees or bushes in the kink region, a direct stroke of the golf ball 9 into the hole 7 on the green 6 is prevented.

The golf player 13 uses the alignment aid in accordance with the invention to reach the first directional point 3 in an optimum manner with the first golf stroke S1 from the teeing ground 2. In this respect, a conspicuous object 8, for instance a tree, in the direction of the first directional point 3 can be marked for the optical direction finding or the GPS coordinates of a conspicuous object for the GPS direction finding are known.

At the first directional point 3, the golfer 13 again uses the alignment aid in accordance with the invention for optimum success to propel the golf ball 9 by a second golf stroke 52 ideally to the hole 7 on the green 6.

Figure 3:
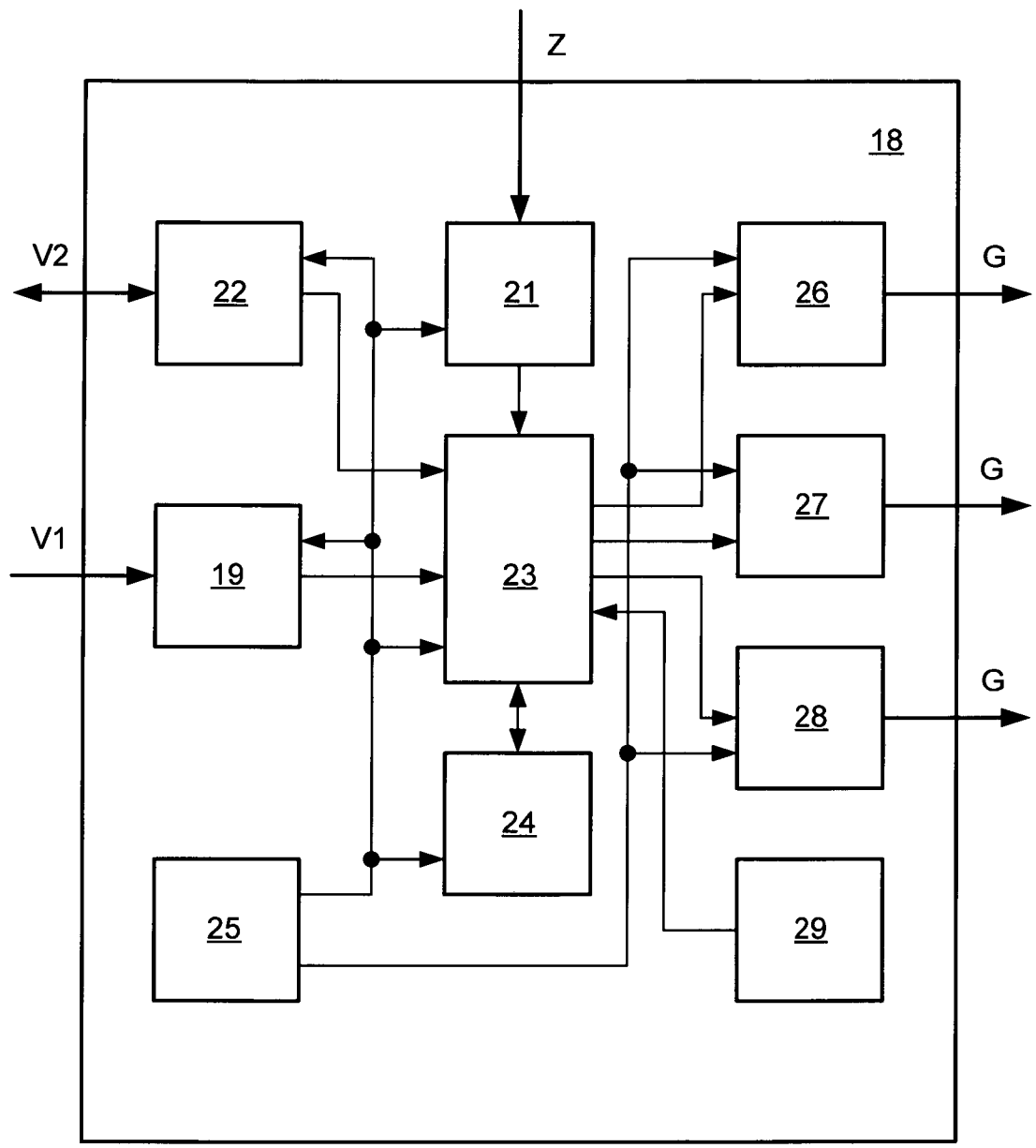
FIG. 3 is a schematic diagram of an embodiment of a handheld device of the alignment aid in accordance with the invention.

FIG. 3 shows in a schematic diagram an embodiment of the handheld device 18 which has a power supply 25.

The determination of the target vector V1 takes place over the direction finding device 19 either by optical direction finding of the target position Z of the hole 7 or by GPS direction finding of the target position Z via the GPS reception device 21. The target vector V1 is then stored in the memory 24 of the handheld device 18. The position vector V2 is received by the first and second sensor systems 30, 31 via the first transmission/reception device 22 and is also saved in the memory 24 of the handheld device 18.

The processing system 23 accesses the memory 24 to obtain the data of the target vector and of the position vector. The included angle a between the target vector V1 and the position vector V2 is determined and its angular dimension is checked using the data. On a successful check, the processing system 23 outputs a good signal G to the visual signal 26 and/or to the acoustic signal 27 and/or to the vibration signal 28. In this respect, the good signal G can be switched off by an automatic switch-off system after a time or by means of the switch 29.

Figure 4:
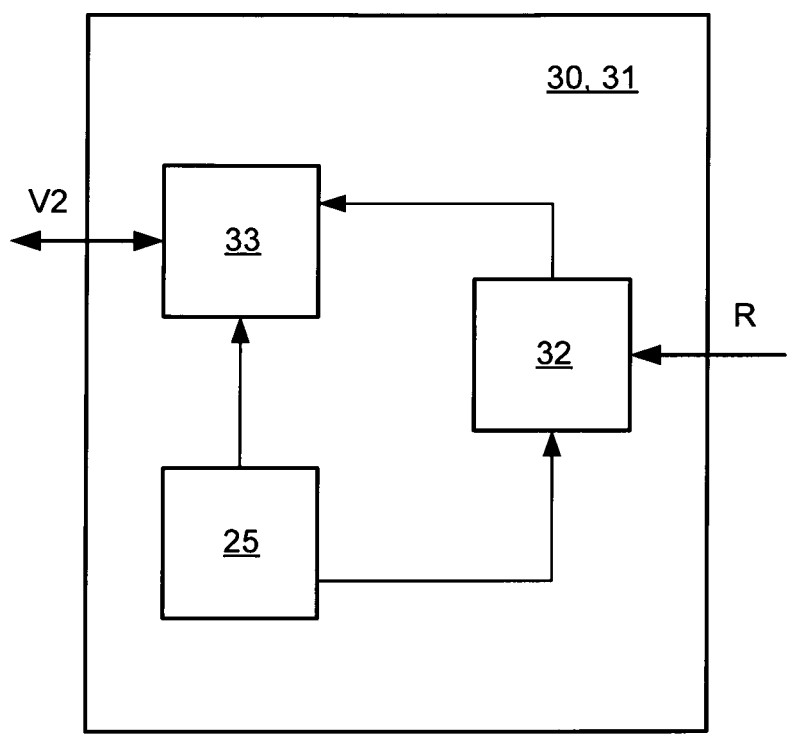
FIG. 4 is a schematic diagram of an embodiment of a measuring device of the alignment aid in accordance with the invention.

FIG. 4 shows in a schematic diagram an embodiment of the first and second sensor systems 30, 31 which can each have a power supply 25 and which together form an example of the aforesaid sensor device.

To transmit the position vector V2 to the handheld device 18, the first and second sensor systems each comprise a second transmission/reception device 33, with the position vector V2 being determined by an exchange of data between the two sensor systems 30, 31. In this respect, the data of the position vector V2 are determined with reference to the relative positions R which are measured by the direction sensor 32 in the first and second sensor systems 30, 31.

REFERENCE NUMERAL LIST

1 course
2 teeing ground
3 first directional point
4 fairway
5.1 sand bunker
5.2 vegetation
6 green
7 hole
8 flagpole
9 golf ball
10 golf club
11 club face
12 shaft
13 golfer
14 first shoe
15 second shoe
16 first heel region
17 second heel region
18 handheld device
19 direction finding device
20 GPS system
21 GPS reception device
22 first transmission/reception device
23 processing system
24 memory
25 power supply
26 visual signal
27 acoustic signal
28 vibration signal
29 switch
30 first sensor system
31 second sensor system
32 direction sensor
33 second transmission/reception device
a angle
A spacing
G good signal
R relative position
S1 first golf stroke
S2 second golf stroke
V1 target vector
V2 position vector
W deviation
Z target position

The invention claimed is:

1. An alignment aid for a golfer, comprising:
an alignment device having a direction finding device for determining a target vector (V1) with respect to a sighted target, the alignment device wearable by the golfer in or at the golfer's body or clothing;
a sensor device for determining a position vector (V2) as a measure of an instantaneous alignment of the golfer, the sensor device disposed in or at the golfer's body or clothing; and
an output device;
the alignment device operable to check an included angle (a) between the target vector (V1) and the position vector (V2) and to automatically output a good signal (G) indicating a successful check of the included angle to the output device upon a successful check of the included angle,
wherein the alignment device, the sensor device and the output device are disposed in or at the golfer's body or clothing thereby enabling hands-free use of alignment aid.

2. The alignment aid in accordance with claim 1, wherein the alignment of a horizontal body line of the golfer is detected by the sensor device.

3. The alignment aid in accordance with claim 1, wherein the sensor device comprises at least two sensor systems which are arranged in or at the body and/or in or at the clothing of the golfer or are in contact therewith when functional.

4. The alignment aid in accordance with claim 3, wherein the two sensor systems are configured to be disposed in or at the shoes or at the lower legs or at the knees or at the hip or at the shoulder of the golfer.

5. The alignment aid in accordance with claim 1, wherein the alignment aid is functional before the striking of a golf ball.

6. The alignment aid in accordance with claim 1, wherein
a first sensor system is arranged in a first shoe and a second sensor system is arranged in a second shoe, the first and second sensor systems each comprise a direction finding sensor for determining a position vector (V2) between the first and second shoes; and
the alignment device comprises:
a memory for storing data from the first and second sensor systems; and
a direction finding device having a direction sensor for determining the target vector (V1) to the sighted target;
the alignment device operable to check the included angle (a) between the target vector (V1) and the position vector (V2).

7. The alignment aid in accordance with claim 1, wherein the output device is operable to provide a visual signal, an acoustic signal and/or a vibration signal.

8. The alignment aid in accordance with claim 1, wherein the direction finding device comprises a direction finding rod or a direction marking.

9. The alignment aid in accordance with claim 1, wherein the direction finding device includes a GPS reception device via which the target vector (V1) to the sighted target is formed.

10. The alignment aid in accordance with claim 6, wherein the direction sensor is a microelectromechanical vibratory gyroscope.

11. The alignment aid in accordance with claim 6, wherein the first and second sensor systems are arranged in a first and second heel region or in a heel of the first and second shoes.

12. The alignment aid in accordance with claim 6, wherein data from the direction finding device is stored in the memory of the alignment device.

13. The alignment aid in accordance with claim 6, wherein
the alignment device comprises a first transmission/reception device for exchanging data over radio with the first and second sensor systems; and
the first and second sensor systems each comprise a second transmission/reception device for exchanging data over radio between the first and second sensor systems and with the alignment device.

14. The alignment aid in accordance with claim 1, wherein the good signal is not output to the output device at the time of the striking of the golf ball.

15. The alignment aid in accordance with claim 14, wherein the alignment device has a switch for switching off the good signal and/or has a time-controlled automatic switch-off system for switching off the good signal.

16. A method of checking an included angle (a) between a target vector (V1) and a position vector (V2), comprising:
(i) providing an alignment aid in accordance with claim 1 and supporting the alignment aid in or at the golfer's body or clothing;
(ii) aligning the direction finding device of the alignment device to a target or determining a direction to the target by GPS;
(iii) receiving a target vector (V1) from the direction finding device of the alignment device or of the GPS;
(iv) receiving a position vector (V2) from the sensor device of the alignment aid;
(v) storing the target vector (V1) and the position vector (V2) in a memory of the alignment device:
(vi) aligning first and second shoes of a golfer in parallel with the target vector (V1);
(vii) determining the included angle (a) between the target vector (V1) and the position vector (V2) in a processing system of the alignment device;
(viii) checking the included angle (a) in a processing system:
(ix) further aligning the two shoes in parallel with the vector (V1) until the included angle (a) becomes equal to zero; and
(x) outputting a good signal indicating a successful check to the output device of the alignment device upon the successful check,
wherein the alignment device, the sensor device and the output device are disposed in or at the golfer's body or clothing thereby enabling hands-free use of alignment aid.

* * * * *